(12) United States Patent
Wu et al.

(10) Patent No.: US 6,201,003 B1
(45) Date of Patent: Mar. 13, 2001

(54) PESTICIDAL 1-ARYLPYRAZOLES

(75) Inventors: Tai-Teh Wu, Chapel Hill; David Treadway Manning, Cary, both of NC (US)

(73) Assignee: Rhone-Poulenc Inc., Research Triangle Park, NC (US)

( * ) Notice: Subject to any disclaimer, the term of this patent is extended or adjusted under 35 U.S.C. 154(b) by 0 days.

(21) Appl. No.: 09/516,231

(22) Filed: Mar. 1, 2000

Related U.S. Application Data

(62) Division of application No. 09/036,788, filed on Mar. 9, 1998, now Pat. No. 6,057,354.
(60) Provisional application No. 60/040,136, filed on Mar. 10, 1997.

(30) Foreign Application Priority Data

Mar. 5, 1998 (WO) .................................. PCT/EP98/01225

(51) Int. Cl.$^7$ ........................ A61K 31/415; C07D 405/04
(52) U.S. Cl. ........................ 514/404; 514/407; 548/365.1
(58) Field of Search ........................ 548/365.1; 514/404, 514/407

(56) References Cited

U.S. PATENT DOCUMENTS

| | | | |
|---|---|---|---|
| 4,614,533 | 9/1986 | Schallner et al. | 548/377 |
| 4,804,675 | 2/1989 | Jensen-Korte et al. | 514/407 |
| 4,810,720 | 3/1989 | Jensen-Korte et al. | 514/407 |
| 5,047,550 | 9/1991 | D'Silva | 548/365 |
| 5,079,370 | 1/1992 | D'Silva et al. | 548/365 |
| 5,104,994 | 4/1992 | Roberts et al. | 548/376 |
| 5,187,185 | 2/1993 | Outcalt et al. | 514/408 |
| 5,223,525 | 6/1993 | Wu et al. | 514/398 |
| 5,232,940 | 8/1993 | Hatton et al. | 514/407 |
| 5,306,694 | 4/1994 | Phillips et al. | 504/252 |
| 5,321,040 | 6/1994 | Huang et al. | 514/407 |
| 5,580,843 | 12/1996 | Stetter et al. | 514/341 |

FOREIGN PATENT DOCUMENTS

| | | |
|---|---|---|
| 195 18 054 | 9/1996 | (DE) . |
| 0154115 | 9/1985 | (EP) . |
| 0201852 | 11/1986 | (EP) . |
| 0295117 | 12/1988 | (EP) . |
| 0352944 | 1/1990 | (EP) . |
| 0403309 | 12/1990 | (EP) . |
| 0418016 | 3/1991 | (EP) . |
| 0659745 | 6/1995 | (EP) . |
| 87/03781 | 7/1987 | (WO) . |
| 93/06089 | 4/1993 | (WO) . |
| 94/21606 | 9/1994 | (WO) . |

*Primary Examiner*—Jane Fan
(74) *Attorney, Agent, or Firm*—Burns, Doane, Swecker & Mathis, L.L.P.

(57) ABSTRACT

1-Arylpyrazoles of the formula:

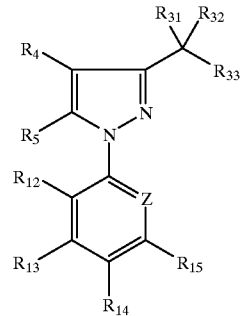

(I)

wherein $R_{31}$, $R_{32}$, $R_{33}$, $R_4$, $R_5$, $R_{12}$, $R_{13}$, $R_{14}$, $R_{15}$ and Z are as defined in the specification, are useful as pesticides or as intermediates to other pesticides. Compositions comprising the compounds of formula (I) and methods for their use, particularly in agriculture and for animal protection, as pesticides, especially for controlling arthropods, are described.

35 Claims, No Drawings

PESTICIDAL 1-ARYLPYRAZOLES

CROSS-REFERENCE TO RELATED APPLICATIONS

This application is a divisional of U.S. patent application Ser. No. 09/036,788, filed Mar. 9, 1998, now U.S. Pat No. 6,057,354, which claims the priority of U.S. Provisional Patent Application Ser. No. 60/040,136, filed Mar. 10, 1997, both of said applications being incorporated by reference herein in their entireties and relied upon.

BACKGROUND OF THE INVENION

1. Field of the Invention

The invention relates to new derivatives of 1-arylpyrazoles which have some valuable properties either as pesticides or as intermediates to make other pesticides. The invention further pertains to compositions of said compounds and methods, using said compounds either as intermediates to make other pesticides, or for the control of arthropod pests, in particular to the application of said compounds or compositions in agricultural methods of use or for animal protection, particularly as pesticides, for controlling arthropods.

2. Description of the Related Art

International Patent Publication No. WO 87/03781 and European Patent Publication Nos. 0295117, 0154115, 0201852 describe insecticidal 1-(substituted phenyl) pyrazoles. Other prior art is also found in the text of these patent applications or the patents issued therefrom.

International Patent Publication Nos. WO 93/06089 and WO 94/21606 also describe insecticidal 1-(4-SF$_5$ substituted phenyl) heterocycles which may be pyrroles as well as imidazoles or pyrazoles. The teaching of these patents is not substantially different from International Patent Publication No. WO 87/03781 or from European Patent Publication No. 0295117 as far as pyrazoles are concerned.

Various pesticidal pyrazoles have been disclosed in various patents or patent applications: European 0418016, 0403309, 0352944; U.S. Pat. Nos. 5,104,994, 5,079,370, 5,047,550, 5,232,940, 4,810,720, 4,804,675, 5,306,694, 4,614,533, 5,187,185, 5,223,525; WO 93/06089, 94/21606.

Due to the many existing pests and crops and conditions of attacks of crops by pests, there is a need for further novel pesticidal compounds.

OBJECTS AND SUMMARY OF THE INVENTION

It is an object of the present invention to provide new pesticidal compounds of the 1-arylpyrazole family together with processes for their preparation.

A second object of the present invention is to provide pesticidal compositions and pesticidal methods of use of the pesticidal pyrazole compounds against arthropods, especially insects, particularly in agricultural or horticultural crops, forestry, veterinary medicine or livestock husbandry, or in public health.

A third object of the present invention is to provide very active compounds, with broad spectrum pesticidal activity, as well as compounds with selective special activity, e.g., aphicidal, miticidal, foliar insecticidal, soil insecticidal, systemic, antifeeding or pesticidal activity via seed treatment.

These and other objects, which are met in whole or in part by the instant invention, shall become readily apparent from the description of the invention which follows.

This invention embraces novel chemical compounds having an insecticidal, miticidal, nematocidal or anthelminthic activity.

The invention relates to compounds having the general formula (I):

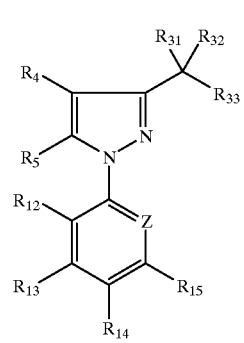

(I)

wherein:

$R_{31}$ and $R_{32}$ may individually be $OR_{20}$, $S(O)_nR_{20}$, or $N(R_{20})(R_{21})$; or $R_{31}$ and $R_{32}$ may also connect to form $O[C(R_{22})(R_{23})]_mO$, $S(O)_n[C(R_{22})(R_{23})]_mS(O)_a$, $O(CH_{21})_mS(O)_n$, $O[C(R_{22})(R_{23})]_m(NR_{20})$, $S(O)_n[C(R_{22})(R_{23})]_m(NR_{20})$, $NR_{21}[C(R_{22})(R_{23})]_mNR_{20}$, $NR_{21}[C(O)(CH_2)_m]NR_{20}$;

m is an integer from 1 to 5;

when m is greater than one, the groups $[C(R_{22})(R_{23})]$ may be the same or different;

$R_{20}$, $R_{21}$ may individually be H, alkyl, aryl, benzyl, allyl, propargyl;

$R_{22}$, $R_{23}$ may individually be H; halogen; OH; $NH_2$; $COOR_{20}$; $C(O)NH_2$; $C(O)N(R_{20})(R_{21})$; $C(S)NH_2$; $OC(O)N(R_{20})(R_{21})$; CN; $NO_2$; $C(S)N(R_{20})(R_{21})$; alkyl which may optionally be substituted with OH, $NH_2$, halogen, CN, $NO_2$, $COOR_{20}$, $C(O)NH_2$, $C(S)NH_2$; $S(O)_b$alkyl; alkoxy; $S(O)_cR_{20}$;

$R_4$ is $R_{26}$; $S(O)_dR_{26}$; $S(=R_{27})(=NR_{28})R_{26}$;

$R_{26}$ is alkyl optionally substituted with one or more halogen which may be the same or different;

$R_5$ is $NH_2$, alkylamino where the alkyl may be substituted with $NO_2$, halogen, CN, alkoxycarbonyl, OH, alkoxy, alkylthio, alkylsulfmyl, alkylsulfonyl or carbamoyl; or $R_5$ is a radical having the formula:

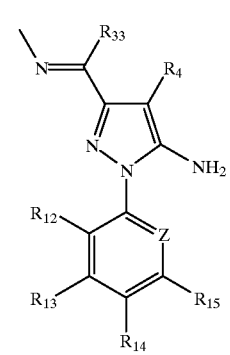

(Ia)

wherein $R_4$, $R_{12}$, $R_{13}$, $R_{14}$, $R_{15}$, Z and $R_{33}$ are identical to $R_4$, $R_{12}$, $R_{13}$, $R_{14}$, $R_{15}$, Z and $R_{33}$, respectively, in formula (I) above;

$R_{27}$ is $NR_{28}$, O or a lone pair of electrons;

$R_{28}$ is selected from H; $C_1$–$C_6$ alkyl; $C_1$–$C_6$ haloalkyl; $COR_{24}$; $S(O)_eR_{24}$; $COOR_{24}$; $C(O)N(R_{20})(R_{21})$; $C(O)SR_{24}$; $C(S)OR_{24}$; $SO_2NR_{20}R_{21}$; $P(O)_q(R_{20})(R_{21})$; $P(O)_q(OR_{20})(OR_{21})$; $C(=NR_{20})NR_{20}R_{21}$; $C(=NR_{20})(OR_{21})$; $C(S)N(R_{20})(R_{21})$; $C(O)C(O)R_{20}$; $C(O)C(O)OR_{20}$; $C(O)C(O)NR_{20}R_{21}$; and $C(O)NR_{20}SO_2R_{21}$;

q is 0 or 1;

$R_{24}$ is alkyl optionally substituted with $NO_2$, CN, halogen, alkoxy, amino, alkoxycarbonyl or OH;

Z is N or C—$R_{16}$;

$R_{12}$, $R_{13}$, $R_{14}$, $R_{15}$ and $R_{16}$ may individually be H; halogen; $SF_5$; CN; $NO_2$; $R_{25}$; $S(O)_fR_{25}$; OH; $OR_{25}$; $N(R_{36})(R_{37})$; $CON(R_{25})(R_{37})$; $N_3$ (azido);

$R_{36}$ and $R_{37}$ may individually be H, alkyl;

$R_{25}$ may be alkyl optionally substituted with one or more halogen which may be the same or different;

$R_{33}$ is $C_1$ to $C_3$ alkyl, optionally substituted by one or more halogen, $NO_2$, alkoxy, CN, COOH, COO-alkyl, $C(O)NH_2$; and n, a, b, c, d, e and f, which are the same or different, are each 0, 1 or 2; and pesticidally acceptable salts thereof.

DETAILED DESCRIPTION OF THE INVENTION AND PREFERRED EMBODIMENTS

The stereoisomers, e.g. diastereomers and optical isomers, having the formula (I) are included in the invention as well.

In this description, the term 'alkyl' when unqualified generally means a straight- or branched-chain alkyl having from one to six carbon atoms. The term 'aryl' means $C_6$–$C_{10}$ aryl, e.g. phenyl or naphthyl, optionally bearing one or more substituents selected from the group consisting of halogen, $C_1$–$C_6$ alkyl, $C_1$–$C_6$ alkoxy, CN, $NO_2$, $C_1$–$C_6$ haloalkyl and $C_1$–$C_6$ haloalkoxy.

Preferred compounds of formula (I) include those wherein $R_{13}$ and $R_{15}$ are H or halogen; $R_{12}$ is halogen; $R_{16}$ is H or halogen; and/or $R_{14}$ is halogen, SF5, $R_{25}$, $S(O)_fR_{25}$ or $OR_{25}$. Compounds in which $R_{12}$ is chlorine, $R_{13}$ and $R_{15}$ are H, $R_{14}$ is $CF_3$, and Z is C—Cl, are especially preferred.

Compounds of formula (I) wherein $R_4$ is $S(O)_dR_{26}$ and Z is C—$R_{16}$ are also preferred.

The symbol m is preferably 2, 3 or 4, more preferably 2 or 3, most preferably 2.

Other preferred compounds of formula (I) are those wherein:

$R_{26}$ is $CH_3$ or $CH_2CH_3$; Z is C—$R_{16}$; $R_{13}$ and $R_{15}$ are H; $R_{12}$ is halogen; $R_{16}$ is H or halogen; $R_{14}$ is $CF_3$, $OCF_3$ or $SF_5$; and/or $R_{33}$ is $CH_3$.

Still most preferred compounds of formula (I) are those wherein:

$R_{31}$ and $R_{32}$ may individually be $OCH_3$; $OC_2H_5$; $SCH_3$; $SC_2H_5$; $R_{31}$ and $R_{32}$ may also connect to form $OCH_2CH_2O$; $O(CH_2)_3O$; $S(CH_2)_2S$; $S(O)(CH_2)_2O$; $S(O)(CH_2)_2S(O)$; $S(O)_2(CH_2)_2S(O)$; $S(O)_2(CH_2)_2S(O)_2$; $S(CH_2)_2O$; $S(O)(CH_2)_2O$; $S(O)_2(CH_2)_2O$; $O(CH_2)[CH(CH_2OH)]O$; $O(CH_2)[C(CH_2OH)(CH_2OH)]O$; $OCH(COOCH_3)CH(COOCH_3)O$; $OCH(COOC_2H_5)CH(COOC_2H_5)O$; $OCH_2C(COOCH_3)(COOCH_3)CH_2O$; $OCH_2C(COOC_2H_5)(COOC_2H_5)CH_2O$; $OCH_2CH(CH_3)O$; $SCH_2CH_2NH$; $OCH_2CH(CH_2CH_2OH)O$; $OCH_2C(CH_2OH)_2CH_2O$; $OCH_2CH(CH_2SCH_3)O$; or $OCH_2CH(CH_2SOCH_3)O$; particularly when $R_4$ is $S(O)_dR26$; $R_{26}$ is $CH_3$ or $CH_2CH_3$; Z is C—$R_{16}$; $R_{13}$ and $R_{15}$ are H; $R_{12}$ is halogen; $R_{16}$ is H or halogen; $R_{14}$ is $CF_3$, $OCF_3$ or $SF_5$; and $R_{33}$ is $CH_3$.

Preferably, the compounds of formula (I) have one or more of the following features:

$R_{12}$ is halogen;

X is C—Cl;

$R_{13}$ and $R_{15}$ are H;

$R_{14}$ is $CF_3$ or $SF_5$;

$R_5$ is $NH_2$, $CH_3NH$, or $CH_3CH_2NH$;

$R_4$ is $CH_3S(O)$, $CH_3S(O)_2$ or $CH_3S$;

$R_{31}$ and $R_{32}$ are $OCH_3$ or connect to form $OCH_2CH_2O$; $OCH_2CH(CH_3)O$; $S(CH_2)_2S$; $S(O)(CH_2)_2S$; $S(O)(CH_2)_2S(O)$; $S(O)_2(CH_2)_2S(O)_2$; $O(CH_2)[CH(CH_2OH)]O$; $SCH_2CH_2NH$; $O(CH_2)CH(CH_2SCH_3)O$; $O(CH_2)CH(CH_2SOCH_3)$.

Compounds of the general formula (I) can be prepared by reacting the compounds of the general formula (II):

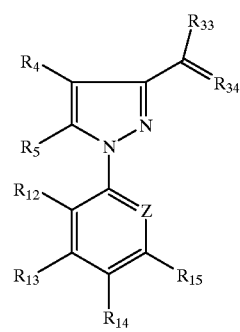

(II)

wherein $R_4$, $R_5$, $R_{12}$, $R_{13}$, $R_{14}$, $R_{15}$, Z and $R_{33}$ are as defined above and $R_{34}$ is oxygen or sulfur, with a compound (III) having at least one reactive functional group selected from the group consisting of alcohol, thiol, primary amine and secondary amine.

More precisely, the compound (III) may be:

an alcohol of general formula of $R_{20}OH$;

a thiol of general formula of $R_{20}SH$;

an amine of general formula of $HN(R_{20})(R_{21})$; or a compound of the formula $HO[C(R_{22})(R_{23})]_mOH$, $HS[C(R_{22})(R_{23})]_mSH$, $HO[C(R_{22})(R_{23})]_mSH$, $HO[C(R_{22})(R_{23})]_mN(R_{20})H$, $HS[C(R_{22})(R_{23})]_mN(R_{20})H$, or $NHR_{20}[C(R_{22})(R_{23})]_mNHR_{21}$ where $R_{22}$ and $R_{23}$ may be the same or different and $R_{20}$ and $R_{21}$, may be the same or different.

The reaction of the compound of (II) with the compound of (III) can be achieved by directly reacting the compounds of formula (II) and the compounds (III) in a liquid medium at a temperature in the range from about −35° C. to about 250° C., preferably from about −10° C. to about 150° C. Removal of water is preferred. The liquid medium can be achieved either by means of the reactant or with a solvent. Possible solvents for the reaction may be organic solvents including alcohols such as methanol, ethanol, isopropanol; ethers such as diethyl ether, tetrahydrofuran, dioxane, dimethoxyethane; nitriles such as acetonitrile; aromatic solvents such as toluene, benzene, chlorobenzene; haloalkanes such as chloroform, methylene chloride; amides such as dimethylamide; ketones such as acetone, methylisobutylketone; esters such as ethyl acetate. The amount of reactant is generally between about 50% and about 200% what is required by the reaction (except when a reactant is used as solvent, and then the amount of reactant is much higher). The reaction can be conducted with or without presence of acid catalyst. The acid catalyst can be an inorganic acid such as hydrochloric acid, sulfuric acid; an organic acid such as acetic acid, formic acid, p-toluenesulfonic acid; Lewis acids such as iron (III) chloride, ammonium chloride, boron trifluoride, aluminum chloride, zinc iodide, zinc chloride; acidic ion-exchange resin; clays such as Montmorillonite.

In the process described in the preceding paragraph, when $R_5$ is —$NH_2$ and $R_{34}$ is oxygen in the starting material of formula (II), in addition to forming a compound of formula (I) in which $R_5$ is —$NH_2$, there can be produced, by reaction with another molecule of the starting material of formula (II), a compound of formula (I) in which $R_5$ is a radical of formula (Ia) set forth hereinabove. Both products are active as pesticides.

The sulfoxide and sulfone compounds of the formula (I), i.e. the compounds in which n, a, b, c, d, e or f is 1 or 2, can also be prepared by oxidation of the corresponding sulfide using appropriate oxidation reagents including but not limited to peroxide, such as hydrogen peroxide, t-butyl peroxide; peracids such as metachloroperbenzoic acid; acyl nitrates such as acetyl nitrate and other nonperoxide agents such as sodium periodate, sodium perborate, manganese oxide, potassium permanganate, N-bromosuccinimide, preferably hydrogen peroxide and sodium periodate.

In cases, such as in oxyketal sulfide, where mild conditions are required sodium periodate is the preferred sulfoxidation agent.

The following non-limiting Examples illustrate the invention.

EXAMPLE 1

Preparation of 5-amino-1-[2,6-dichloro4-(trifluoromethyl)phenyl]-3-[(1,1-dimethoxy)ethyl]4-methylthio-1H-pyrazole A mixture of 2.0 g (0.0052 mole) of 3-acetyl-5-amino-1-[2,6-dichloro-4-(trifluoromethyl)phenyl]-4-methylthio-1H-pyrazole, 1.7 ml (0.0156 mole) of trimethyl orthoformate, 0.060 g (0.0003 mole) of para-toluenesulfonic acid monohydrate and 10 ml of methanol was heated at 40° C. for about 8 hours, then left 64 h at 20° C. The mixture was mixed with a saturated solution of $NaHCO_3$, extracted with dichloromethane, and successively dried, filtered, evaporated, chromatographed on silica gel. 0.59 g of the title compound having a melting point of about 149° C. was obtained.

EXAMPLE 2

Preparation of 5-amino-1-[(2,6-dichloro-4-(trifluoromethyl)phenyl]-3-(2-methyl-1,3-dioxolane-2-yl)-4-methylthio-1H-pyrazole A mixture of 10.0 g (26.03 mmol) of [2,6-dichloro-4-(trifluoromethyl)phenyl]-3-acetyl-4-methylthio-1H-pyrazole, 1.94 g (31.23 mmol) of 1,2-ethanediol, 0.49 g (2.6 mmol) of p-toluenesulfonic acid and 500 ml of benzene was heated to reflux with removal of water for 10 hr. The mixture was mixed with aqueous sodium bicarbonate. The organic layer was washed with saturated aqueous potassium chloride and then successively dried, evaporated, chromatographed. 2.33 g of the title compound was obtained (melting point about 143° C.).

EXAMPLE 3

Preparation of 5-amino-1-[2,6-dichloro-4-(trifluoromethyl)phenyl]-3-(2-methyl-1,3-dioxolane-2-yl)-4-methylsulfinyl-1H-pyrazole To a solution of 244 microliters of 0.5 M sodium periodate in 2.5 ml of methanol at 0° C. was added 500 mg of the product of EXAMPLE 2. The mixture was stirred at 0° C. for 20 min and then left for 10 hours at 20° C. The mixture was successively extracted with methylene chloride and water, separated, dried, evaporated so as to give the title compound; mass spectral analysis gave M+H=444 (Molecular weight=443).

EXAMPLE 4

Preparation of 5-amino-1-[2,6-dichloro-4-(trifluoromethyl)phenyl]-3-(2-methyl-1,3-dithiolane-2-yl)-4-methylthio-1H-pyrazole A mixture of 1 g (2.60 mmol) of 5-amino-1-[2,6-dichloro-4-(trifluoromethyl)phenyl]-3-acetyl-4-methylthio-1H-pyrazole, 0.26 ml (3.10 mmol) of 1,2-ethanedithiol, 0.084 g (0.5 mmol) of iron(III) chloride and 25 ml of methylene chloride was stirred at 20° C. under an inert atmosphere for 6 days. The mixture was evaporated and chromatographed so as to give 100 mg of yellow oil of the title compound. Mass spectral analysis gave a molecular weight of 460.

EXAMPLE 5

Preparation of 5-amino-1-[2,6-dichloro-4-(trifluoromethyl)phenyl]-3-(2-methylthiazolidine-2-yl)-4-methylsulfinyl-1H-pyrazole A mixture of 1 g (2.5 mmol) of 5-amino-1-[2,6-dichloro-4-(trifluoromethyl)phenyl]-3-acetyl4-methylsulfinyl-1H-pyrazole, 0.284 g (2.5 mmol) of 2-aminoethanethiol hydrochloride, 348 microliters (2.50 mmol) of triethylamine, 50 mg of p-toluenesulfonic acid and 30 ml of benzene was heated to reflux with removal of water overnight. The mixture was successively cooled, filtered, evaporated, chromatographed so as to give 20 mg of the title compound as white solid; melting point 85° C.

EXAMPLE 6

Preparation of 5-amino-1-[2,6-dichloro-4-(trifluoromethyl)phenyl]-3-(2-methyl-1,3-oxathiolane-2-yl)-4-methylsulfonyl-1H-pyrazole To a stirred solution of 54.34 grams (0.131 mole) of 3-acetyl-5-amino-1-[2,6-dichloro4-(trifluoromethyl)phenyl]-4-methylsulfonyl-1H-pyrazole in 500 mL of dioxane was added, in sequence, 36.7 mL (0.522 mole) of mercaptoethanol, 71.1 grams (0.522 mole) of anhydrous zinc chloride and 62.1 grams (0.522 mole) of anhydrous sodium sulfate while cooling at 0° C. in an ice bath. The mixture was then stirred for a period of approximately 17 hours while allowing it to warm to room temperature. The mixture was filtered to remove salts and the filtrate concentrated under reduced pressure and diluted with 40 mL of acetonitrile, collecting the product by filtering at 35° C. The filtrate was further diluted with acetonitrile to obtain a second crop of product. The combined crops of 5-amino-1-[2,6-dichloro-4-(trifluoromethyl)phenyl]-3-(2-methyl-1,3-oxathiolane-2-yl)4-methylsulfonyl-1H-pyrazole gave 30.53 grams of material, having a melting point of 201° C. This compound is hereinafter referred to as Compound No. 23.

EXAMPLE 7

Preparation of 5-amino-1-[2,6-dichloro-4-(trifluoromethyl)phenyl]-3-(2-methyl-1,1,3,3-tetraoxo-1,3-dithiolane-2-yl)-4-methylsulfonyl-1H-pyrazole To an ice-cooled solution of 0.49 gram (0.00096 mole) of 5-amino-1-[2,6-dichloro-4-(trifluoromethyl)phenyl]-3-(2-methyl-1-oxo-1,3-dithiolane-2-yl)-4-methylsulfonyl-1H-pyrazole in 4 mL of trifluoroacetic acid was added 0.4 mL (0.004 mole) of 30% hydrogen peroxide, dropwise, and the mixture stirred while allowing it to warm to room temperature for an approximate 17-hour period. The mixture was partitioned between ethyl acetate and water and the organic phase separated, washed with saturated aqueous sodium bicarbonate, then brine, and dried over sodium sulfate. The solution was filtered, concentrated under reduced pressure, and chromatographed on silica gel to give 0.14 gram of 5-amino-1-[2,6-dichloro-4-(trifluoromethyl)phenyl]-3-(2-methyl-1,1,3,3-tetraoxo-1,3-dithiolane-2-yl)-4-methylsulfonyl-1H-pyrazole as a cream colored powder having a melting point of 231° C. This compound is hereinafter referred to as Compound No. 25.

EXAMPLE 8

Preparation of 1-[2,6-dichloro-4-(trifluoromethyl)phenyl]-4-methylthio-3-(4-bydroxymetyl-2-metbyl-1,3-dioxolan-2-yl)-5-N-1-[[[2,6-dichloro-4-(trifluoromethly)phenyl]-4-methylthio-1H-pyrazol-3-yl]ethylidene]amino-1H-pyrazole In the synthesis of Compound No. 6, Table 1, by the condensation of 3-acetyl-5-amino-1-[2,6-dichloro-4-(trifluoromethyl)phenyl]-4-methylthio-1H-pyrazole with glycerol, employing the procedure of Example 2, above, working up the reaction mixture resulted in isolation of 1-[2,6-dichloro-4-(trifluoromethyl)phenyl]-4-methylthio-3-(4-hydroxymethyl-2-methyl-1,3-dioxolan-2-yl)-5-N-1-[[[2,6-dichloro-4-(trifluoromethyl)phenyl]-4-methylthio-1H-pyrazol-3-yl]ethylidene]amino-1H-pyrazole as a by-product having a melting point of 100° C. This compound is referred to hereinafter as Compound No. 9.

The following compounds were prepared according one of the processes described in the Examples 1 to 8:

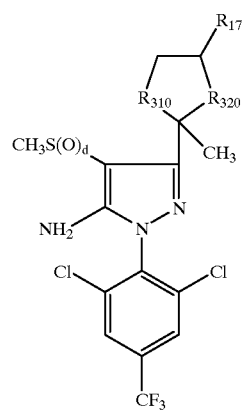

| Compound | $R_{31}$ | $R_{32}$ | d | melting point |
|---|---|---|---|---|
| 1 | $OCH_3$ | $OCH_3$ | 0 | 149 |
| 2 | $OCH_3$ | $OCH_3$ | 1 | 153 |

-continued

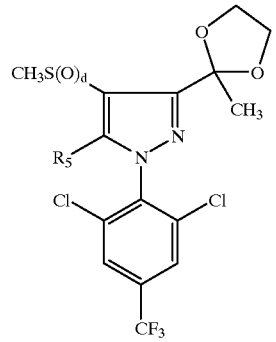

| Compound | $R_{310}$ | $R_{320}$ | $R_{17}$ | d | melting point |
|---|---|---|---|---|---|
| 3 | O | O | H | 0 | 100 |
| 4 | O | O | $CH_3$ | 0 | 126 |
| 5 | O | O | H | 2 | 194 |
| 6 | O | O | $CH_2OH$ | 0 | 71 |
| 7 | O | O | $CH_2OH$ | 2 | 183 |
| 8 | O | O | $CH_3$ | 2 | 202 |
| 10 | O | O | H | 1 | 68 |
| 11 | O | O | $CH_3$ | 1 | 90 |
| 15 | S | NH | H | 1 | 85 |
| 16 | S | S | H | 0 | $(M + H)^+ = 460$ |
| 17 | S | S | H | 2 | 207 |
| 18 | S | S | H | 1 | 127 |
| 19 | SO | S | H | 0 | 179.5 |
| 20 | SO | S | H | 1 | 182 |
| 21 | SO | S | H | 2 | 195 |
| 22 | SO | SO | H | 2 | 175 |
| 23 | S | O | H | 2 | 201 |
| 24 | S | O | H | 0 | $(M + H) + = 444$ |
| 25 | $SO_2$ | $SO_2$ | H | 2 | 231 |
| 26 | O | O | $CH_2OH$ | 1 | 153 |
| 27 | O | O | $CH_2SCH_3$ | 0 | 43 |
| 28 | O | O | $CH_2SOCH_3$ | 0 | 68 |
| 29 | O | O | $CH_2SOCH_3$ | 1 | 82 |
| 30 | O | O | $CH_2SCH_3$ | 2 | 68 |
| 31 | O | O | $CH_2SOCH_3$ | 2 | 110 |

| Compound | $R_5$ | d | Melting Point |
|---|---|---|---|
| 34 | EtNH | 2 | 119 |
| 35 | MeNH | 2 | 188 |
| 36 | EtNH | 0 | $(M + H)^+ = 456$ |
| 37 | EtNH | 1 | $(M + H)^+ = 472$ |
| 38 | MeNH | 0 | $(M + H)^+ = 442$ |
| 39 | MeNH | 1 | $(M + H)^+ = 458$ |

-continued

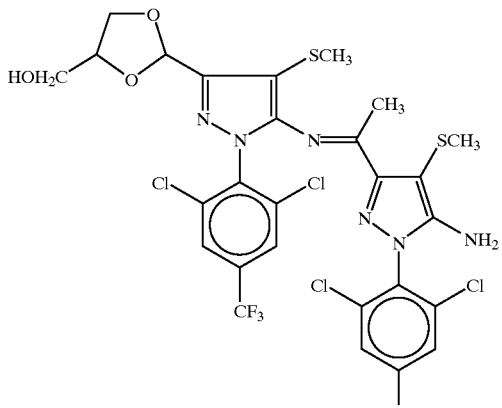

Compound 9

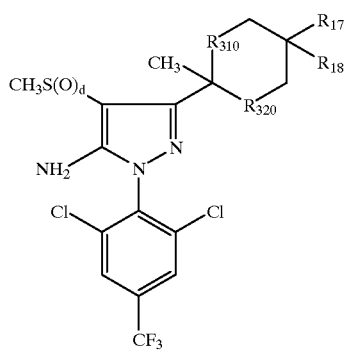

| Compd | $R_{310}$ | $R_{320}$ | $R_{17}$ | $R_{18}$ | d | M.P. |
|---|---|---|---|---|---|---|
| 12 | O | O | H | H | 0 | 143 |
| 13 | O | O | H | H | 2 | 223 |
| 14 | O | O | $CH_2OH$ | $CH_2OH$ | 0 | 85 |

The present invention further provides a method of control of pests at a locus which comprises the treatment of the locus (e.g., by application or administration) with an effective amount of a compound of formula (I) or a pesticidally acceptable salt thereof, wherein the substituent groups are as hereinbefore defined. The locus, includes, for example, the pest itself or the place (plant, animal, field, structure, premises, forest, orchard, waterway, soil, plant or animal product, or the like) where the pest resides or feeds.

In particular, the present invention provides a method for the systemic control of arthropods at a locus, especially some insects or mites which feed on the above-ground portions of plants. Control of such foliar pests may be provided by direct foliar application or by application by, for example, soil spray or granule application to the plant roots or plant seeds with subsequent systemic translocation to the above-ground portions of the plants. Such systemic activity includes the control of insects which reside not only at the point of application but at a remote part of the plant, for example, by translocation from one side of a leaf to the other or from a treated leaf to an untreated leaf. Examples of the classes of insect pests which may be systemically controlled by the compounds of the invention include the Homptera order (piercing-sucking), H raipter order (piercing-sucking), and Thysanopkera order. The invention is especially appropriate for aphids and thrips.

As is evident from the foregoing pesticidal uses, the present invention provides pesticidally active compounds and methods of use of said compounds for the control of a number of pest species which includes: arthropods, especially insects or mites; plant nematodes; or helminth or protozoan pests. The compounds of formula (I) or pesticidally acceptable salts thereof thus are advantageously employed in practical uses, for example, in agricultural or horticultural crops, forestry, veterinary medicine or livestock husbandry, or in public health. From this point forward, whenever the term "compounds of formula (I)" is used this term embraces compounds of formula (I) and their pesticidally acceptable salts. The term "compound of formula (I)" embraces a compound of formula (I) and a pesticidally acceptable salt thereof.

The compounds of this invention may in addition be used to control soil insects, such as corn rootworm, termites (especially for protection of structures), root maggots, wireworms, root weevils, stalkborers, cutworms, root aphids, or grubs. They may also be used to provide activity against plant pathogenic nematodes, such as root-knot, cyst, dagger, lesion, or stem or bulb nematodes, or against mites. For the control of soil pests, for example corn rootworm, the compounds are advantageously applied to or incorporated at an effective rate into the soil in which crops are planted or to be planted or to the seeds or growing plant roots.

In the area of public health, the compounds are especially useful in the control of many insects, especially filth flies or other Dipteran pests, such as houseflies, stableflies, soldierflies, hornflies, deerflies, horseflies, midges, punkies, blackflies, or mosquitoes.

Compounds of the invention may be used in the following applications and on the following pests including arthropods, especially insects or mites, nematodes, or helminth or protozoan pests:

In the protection of stored products, for example cereals, including grain or flour, groundnuts, animal feedstuffs, timber or household goods, e.g. carpets and textiles, compounds of the invention are useful against attack by arthropods, more especially beetles, including weevils, moths or mites, for example Ephestia spp. (flour moths), Anthrenus spp. (carpet beetles), Tribolium spp. (flour beetles), Sitophilus spp. (grain weevils) or Acarus spp. (mites).

In the control of cockroaches, ants or termites or similar arthropod pests in infested domestic or industrial premises or in the control of mosquito larvae in waterways, wells, reservoirs or other running or standing water.

For the treatment of foundations, structures or soil in the prevention of the attack on building by termites, for example, Reticulitermes spp., Heterotermes spp., Coptotermes spp.

In agriculture against adults, larvae and eggs of Lepidoptera (butterflies and moths), e.g. Heliothis spp. such as Heliothis virescens (tobacco budworm), Heliothis armigera and Heliothis zea. Against adults and larvae of Coleoptera (beetles) e.g. Anthonomus spp. e.g. grandis (cotton boll weevil), Letinotarsa decemlineata (Colorado potato beetle), Diabrotica spp. (corn rootworms). Against, Heteroptera (Hemiptera and Homoptera) e.g. Psylla spp., Bemisia spp., Trialeurodea spp., Aphis spp., Myzus spp., *Megoura viciae*, .Phylloxera spp., Nephoettix spp. (rice leaf hoppers), Nilaparvata spp.

Against Diptera e.g. Musca spp. Against Thysanoptera such as Thrips tabaci. Against Orthoptera such as Locusta and Schistocerca spp. (locusts and crickets) e.g. Gryllus spp., and Acheta spp. for example, *Blatta orientalis*

*Periplaneta americana, Blatella germanica, Locusta migratoria migratoriodes*, and *Schistocerca gregaria*. Against Collembola e.g. Periplaneta spp. and Blattela spp. (roaches). Against Isoptera e.g. Coptotermes spp. (termites).

Against arthropods of agricultural significance such as Acari (mites) e.g. Tetranychus spp., and Panonychus spp.

Against nematodes which attack plants or trees of importance to agriculture, forestry or horticulture either directly or by spreading bacterial, viral, mycoplasma or fungal diseases of the plants, for example root-knot nematodes such as Meloidogyne spp. (e.g. *M. incognita*).

In the field of veterinary medicine or livestock husbandry or in the maintenance of public health against arthropods, helminths or protozoa which are parasitic internally or externally upon vertebrates, particularly warm-blooded vertebrates, for example domestic animals, e.g. cattle, sheep, goats, equines, swine, poultry, dogs or cats, for example Acarina, including ticks e.g. Ixodes spp., Boophilus spp. e.g. *Boophilus microplus*, Rhipicelphalus spp. e.g. *Rhipicehalus appendiculatus*, Ornithodorus spp. (e.g. Ornithodorus moubata and mites (e.g. Damalinia spp.); Diptera (e.g. Aedes spp., Anopheles spp., Musca spp., Hypoderma spp.); Hemiptera.; Dictyoptera (e.g. Periplaneta spp., Blatella spp.); Hymenoptera; for example against infections of the gastrointestinal tract caused by parasitic nematode worms, for example members of the family Trichostrongylidae; in the control and treatment of protozoal diseases caused by, for example, Eimeria spp. e.g. *Trypanosoms cruzi*, Leishaminia spp., Plasmodium spp., Babesis spp., Trichomoadidae spp., Toxoplasma spp. and Theileria spp.

In practical use for the control of arthropods, especially insects or mites, or nematode pests of plants, a method, for example, comprises applying to the plants or to the medium in which they grow an effective amount of a compound of the invention. For such a method, the active compound is generally applied to the locus in which the arthropod or nematode infestation is to be controlled at an effective rate in the range of about 5 g to about 1 kg of the active compound per hectare of locus treated. Under ideal conditions, depending on the pest to be controlled, a lower rate may offer adequate protection. On the other hand, adverse weather conditions, resistance of the pest or other factors may require that the active ingredient be users at higher rates. The optimum rate depends usually upon a number of factors, for example, the type of pest being controlled, the type or the growth stage of the infested plant, the row spacing or also the method of application. More preferably an effective rate range of the active compound is from about 50 g/ha to about 400 g/ha.

When a pest is soil-borne, the active compound, generally in a formulated composition, is distributed evenly over the area to be treated (i.e., for example broadcast or band treatment) in any convenient manner and is applied at rates from about 5 g to about 1 kg ai/ha, preferably from about 50 to about 250 g ai/ha. When applied as a root dip to seedlings or drip irrigation to plants, the liquid solution or suspension contains from about 0.075 to about 1000 mg ai/l, preferably from about 25 to about 200 mg ai/l. Application may be made, if desired, to the field or crop-growing area generally or in close proximity to the seed or plant to be protected from attack. The active component can be washed into the soil by spraying with water over the area or can be left to the natural action of rainfall. During or after application, the formulated compound can, if desired, be distributed mechanically in the soil, for example by ploughing, disking, or use of drag chains. Application can be prior to planting, at planting, after planting but before sprouting has taken place, or after sprouting.

The compounds of the invention and methods of control of pests therewith are of particular value in the protection of field, forage, plantation, glasshouse, orchard or vineyard crops, of ornamentals, or of plantation or forest trees, for example: cereals (such as wheat or rice), cotton, vegetables (such as peppers), field crops (such as sugar beets, soybeans or oil seed rape), grassland or forage crops (such as maize or sorghum), orchards or groves (such as of stone or pit fruit or citrus), ornamental plants, flowers or vegetables or shrubs under glass or in gardens or parks, or forest trees (both deciduous and evergreen) in forests, plantations or nurseries.

They are also valuable in the protection of timber (standing, felled, converted, stored or structural) from attack, for example, by sawflies or beetles or termites.

They have applications in the protection of stored products such as grains, fruits, nuts, spices or tobacco, whether whole, milled or compounded into products, from moth, beetle, mite or grain weevil attack. Also protected are stored animal products such as skins, hair, wool or feathers in natural or converted form (e.g. as carpets or textiles) from moth or beetle attack as well as stored meat, fish or grains from beetle, mite or fly attack.

Additionally, the compounds of the invention and methods of use thereof are of particular value in the control of arthropods, helminths or protozoa which are injurious to, or spread or act as vectors of diseases in domestic animals, for example those hereinbefore mentioned, and more especially in the control of ticks, mites, lice, fleas, midges, or biting, nuisance or myiasis flies. The compounds of the invention are particularly useful in controlling arthropods, helminths or protozoa which are present inside domestic host animals or which feed in or on the skin or suck the blood of the animal, for which purpose they may be administered orally, parenterally, percutaneously or topically.

Furthermore, compounds of the invention may be useful for coccidiosis, a disease caused by infections from protozoan parasites of the genus Eimeria. It is an important potential cause of economic loss in domestic animals and birds, particularly those raised or kept under intensive conditions. For example, cattle, sheep, pigs or rabbits may be affected, but the disease is especially important in poultry, particularly in chickens. Administration of a small amount of a compound of the invention, preferably by a combination with feed is effective in preventing or greatly reducing the incidence of coccidiosis. The compounds are effective against both the cecal form and the intestinal forms. Furthermore, the compounds of the invention may also exert an inhibiting effect on oocytes by greatly reducing the number and sporulation of those produced. The poultry disease is generally spread by the birds picking up the infectious organism in droppings in or on contaminated litter, ground, food, or drinking water. The disease is manifested by hemorrhage, accumulation of blood in the ceca, passage of blood to the droppings, weakness and digestive disturbances. The disease often terminates in the death of the aniinal, but the fowl which survive severe infections have had their market value substantially reduced as a result of the infection.

The compositions hereinafter described for application to growing crops or crop growing loci or as a seed dressing may, in general, alternatively be employed for topical application to animals or in the protection of stored products, household goods, property or areas of the general environment. Suitable means of applying the compounds of the invention include:

to growing crops as foliar sprays, dusts, granules, fogs or foams or also as suspensions of finely divided or encapsulated compositions as soil or root treatments by liquid drenches, dusts, granules, smokes or foams; to seeds of crops via application as seed dressings by liquid slurries or dusts;

to animals infested by or exposed to infestation by arthropods, hehminths or protozoa, by parenteral, oral or topical application of compositions in which the active ingredient exhibits an immediate and/or prolonged action over a period of time against the arthropods, helninths or protozoa, for example by incorporation in feed or suitable orally-ingestible pharmaceutical formulations, edible baits, salt licks, dietary supplements, pour-on formulations, sprays, baths, dips, showers, jets, dusts, greases, shampoos, creams, wax smears or livestock self-treatment systems;

to the environment in general or to specific locations where pests may lurk, including stored products, timber, household goods, or domestic or industrial premises, as sprays, fogs, dusts, smokes, wax-smears, lacquers, granules or baits, or in tricklefeeds to waterways, wells, reservoirs or other running or standing water;

to domestic animals in feed to control fly larvae feeding in their feces.

The following non-limiting examples illustrate the use of the compounds of the invention in controlling pests.

The species tested were as follows:

| GENUS, SPECIES | COMMON NAME |
| --- | --- |
| Aphis gossypii | cotton leaf aphid |
| Musca domestica | housefly |
| Diabrotica virgifera | Western cornrootworm |
| Periplaneta americana | American Cockroaches |
| Spodoptera eridania | Southern armyworm |
| Schizaphis graminum | greenbug |
| Ctenocephalides felis | Cat flea |
| Rhipicephalus sanguineus | Brown dog tick |

The Soil Drench Test (Systemic Activity)

Cotton and sorghum plants were established in pots. One day prior to treatment, each pot was infested with about 25 aphids of a mixed population. Cotton plants were infested with aphids and sorghum plants were infested with the greenbug. The selected compound of formula (I) was applied to the soil surface in a dilution that delivered the equivalent of 10.0 ppm soil concentration by weight. Aphid counts were obtained at 5 DAT (=days after treatment). The number of aphids on the treated plants was compared to the number of those on the untreated control plants. This test shows systemic activity (migration of the active ingredient).

The Housefly Bait/Contact Test

About 25 four to six-day-old adult houseflies were anesthetized and placed in a cage with a sugar water bait solution containing the compound. The concentration of the selected compound of formula (I) in the bait solution was 50 ppm. After 24 hours, flies which showed no movement on stimulation were considered dead.

Foliar application (Contact Test) with Aphids

Aphid-infested cotton plants were placed on a revolving turntable, and sprayed to runoff with a 100 ppm formulation of the selected compound of formula (I). The treated, A. gossypii-infested plants were held for three days after treatment, after which the dead aphids were counted.

The obtained results are as follows. In the table that follows 'X' means highly active; '+' means moderately active; and '−' means low activity.

| Compd. No. | Systemic activity on aphids | Systemic activity on greenbugs | Activity on house flies by contact | Foliar activity on aphids |
| --- | --- | --- | --- | --- |
| 1 | X | X | X | + |
| 2 | + | X | X | X |
| 3 | X | X | X | X |
| 4 | X | X | X | X |
| 5 | X | X | X | X |
| 6 | + | X | − | − |
| 7 | X | X | + | X |
| 8 | X | X | X | X |
| 9 | − | − | X | − |
| 10 | X | X | X | X |
| 11 | X | X | X | X |
| 12 | X | X | X | X |
| 13 |   | X | X | X |
| 14 | − |   | − | − |
| 15 | X | X | X | − |
| 16 | − | X | X | + |
| 17 | X | X | X | + |
| 18 | − | + | X | X |
| 19 | − | + | X | X |
| 20 | − | − | X | − |
| 21 | − | − | X | − |
| 22 | X | + | − | − |
| 23 | X |   | − |   |
| 24 | X | X |   |   |
| 25 | − |   | − |   |
| 26 | − | + | X | − |
| 27 | X | + | X | − |
| 28 | X | − | X | X |
| 29 | X | − | X | X |
| 30 | X |   | − |   |
| 31 | X |   | + | + |
| 32 | X | X | X | X |
| 33 | − | − | − | − |
| 34 | X | X | X | X |
| 35 | X | X | X | X |
| 36 | X |   | X | + |
| 37 | X |   | X | X |
| 38 | X | X | X |   |
| 39 | + | X | − |   |

In practice, the compounds of the invention most frequently form parts of compositions. The invention therefore also relates to a pesticidal composition comprising a compound of formula (I) or a pesticidally acceptable salt thereof, and a pesticidally acceptable carrier. These compositions can be employed to control: arthropods, especially insects or mites; nematodes; or helminth or protozoan pests. The compositions may be of any type known in the art suitable for application to the desired pest in any premises or indoor or outdoor area or by internal or external administration to vertebrates. These compositions contain at least one compound of formula (I) or a pesticidally acceptable salt thereof, such as described earlier, as the active ingredient in combination or association with one or more other compatible components which are, for example, solid or liquid carriers or diluents, adjuvants, surface-active agents, or the like appropriate for the intended use and which are agronomically or medicinally acceptable. These compositions, which may be prepared by any manner known in the art, likewise form a part of this invention.

These compositions may also contain other kinds of ingredients such as protective colloids, adhesives, thickeners, thixotropic agents, penetrating agents, spray oils (especially for acaricidal use), stabilizers, preservative agents (especially mold preservatives), sequestering agents, or the like, as well as other known active ingredients with pesticidal properties (particularly insecticidal, miticidal, nematicidal, or fungicidal) or with properties regulating the growth of plants. More generally, the compounds employed in the invention may be combined with all the solid or liquid additives corresponding to the usual techniques of formulation.

Compositions, suitable for applications in agriculture, horticulture, or the like include formulations suitable for use as, for example, sprays, dusts, granules, fogs, foams, emulsions, or the like.

The effective use doses of the compounds employed in the invention can vary within wide limits, particularly depending on the nature of the pest to be eliminated or degree of infestation, for example, of crops with these pests. In general, the compositions according to the invention preferably contain, particularly for use in agriculture, about 0.05 to about 95% (by weight) of a compound of formula (I) or a pesticidally acceptable salt thereof according to the invention, about 1 to about 95% of one or more solid or liquid carriers and, optionally, about 0.1 to about 50% of one or more other compatible components, such as surface-active agents or the like.

In the present account, the term "carrier" denotes an organic or inorganic ingredient, natural or synthetic, with which the active ingredient is combined to facilitate its application, for example, to the plant, to seeds or to the soil. This carrier is therefore generally inert and it must be acceptable (for example, agronomically acceptable, particularly to the treated plant).

The carrier may be a solid, for example, clays, natural or synthetic silicates, silica, resins, waxes, solid fertilizers (for example ammonium salts), ground natural minerals, such as kaolins, clays, talc, chalk, quartz, attapulgite, montmorillonite, bentonite or diatomaceous earth, or ground synthetic minerals, such as silica, alumina, or silicates especially aluminum or magnesium silicates. As solid carriers for granules the following are suitable: crushed or fractionated natural rocks such as calcite, marble, pumice, sepiolite and dolomite; synthetic granules of inorganic or organic meals; granules of organic material such as sawdust, coconut shells, corn cobs, corn husks or tobacco stalks; kieselguhr, tricalcium phosphate, powdered cork, or absorbent carbon black; water soluble polymers, resins, waxes; or solid fertilizers. Such solid compositions may, if desired, contain one or more compatible wetting, dispersing, emulsifying or coloring agents which, when solid, may also serve as a diluent.

The carrier may also be liquid, for example: water; alcohols, particularly butanol or glycol, as well as their ethers or esters, particularly methylglycol acetate; ketones, particularly acetone, cyclohexanone, methylethyl ketone, methylisobutylketone, or isophorone; petroleum fractions such as paraffinic or aromatic hydrocarbons, particularly xylenes or allyl naphthalenes; mineral or vegetable oils; aliphatic chlorinated hydrocarbons, particularly trichloroethane or methylene chloride; aromatic chlorinated hydrocarbons, particularly chlorobenzenes; water-soluble or strongly polar solvents such as dimethylformamide, dimethyl sulfoxide, or N-methylpyrrolidone; liquefied gases; or the like or a mixture thereof.

The surface-active agent may be an emulsifying agent, dispersing agent or wetting agent of the ionic or non-ionic type or a mixture of such surface-active agents. Among these are e.g., salts of polyacrylic acids, salts of lignosulfonic acids, salts of phenolsulfonic or naphthalenesulfonic acids, polycondensates of ethylene oxide with fatty alcohols or fatty acids or fatty esters or fatty amines, substituted phenols particularly alkylphenols or arylphenols), salts of sulfosuccinic, acid esters, taurine derivatives (particularly alkyltaurates), phosphoric esters of alcohols or of polycondensates of ethylene oxide with phenols, esters of fatty acid, with polyols, or sulfate, sulfonate or phosphate functional derivatives of the above compounds. The presence of at least one surface-active agent is generally essential when the active ingredient and/or the inert carrier are only slightly water soluble or are not water soluble and the carrier agent of the composition for application is water.

Compositions of the invention may further contain other additives such as adhesives or colorants. Adhesives such as carboxymethylcellulose or natural or synthetic polymers in the form of powders, granules or lattices, such as arabic gun, polyvinyl alcohol or polyvinyl acetate, natural phospholipids, such as cephalins or lecithins, or synthetic phospholipids can be used in the formulations. It is possible to use colorants such as inorganic pigments, for example: iron oxides, titanium oxides or Prussian Blue; organic dyestuffs, such as alizarin dyestuffs, azo dyestuffs or metal phthalocyanine dyestuffs; or trace nutrients such as salts of iron, manganese, boron, copper, cobalt, molybdenum or zinc.

Compositions containing compounds of formula (I), or pesticidally acceptable salts thereof, which may be applied to control arthropod, plant nematode, helminth or protozoan pests, may also contain synergists (e.g. piperonyl butoxide or sesamex), stabilizing substances, other insecticides, acaricides, plant nematocides, anthelmintics or anticoccidials, fungicides (agricultural or veterinary as appropriate, e.g. benomyl and iprodione), bactericides, arthropod or vertebrate attractants or repellents or pheromones, deodorants, flavoring agents, dyes, or auxiliary therapeutic agents, e.g. trace elements. These may be designed to improve potency, persistence, safety, uptake where desired, spectrum of pests controlled or to enable the composition to perform other useful functions in the same animal or area treated.

Examples of other pesticidally-active compounds which may be included in, or used in conjunction with the compositions of the present invention are: acephate, chlorpyrifos, demeton-S-methyl, disulfoton, ethoprofos, fenitrothion, fenamiphos, fonofos, isazophos, isofenphos, malathion, monocrotophos, parathion, phorate, phosalone, pirimiphos-methyl, terbufos, triazophos, cyflutlirin, cypermethrin, deltametlrin, fenpropathrin, fenvalerate, permethrin, tefluthrin, aldicarb, carbosulfan, methomyl, oxamyl, pirimicarb, bendiocarb, teflubenzuron, dicofol, endosulfan, lindane, benzoximate, cartap, cyhexatin, tetradifon, avermectins, ivermectins, milbemycins, thiophanate, trichlorfon, dichlorvos, diaveridine or dimetriadazole.

For their agricultural application, the compounds of the formula (I), or pesticidally acceptable salts thereof, are therefore generally in the form of compositions, which are in various solid or liquid forms.

Solid forms of compositions which can be used are dusting powders (with a content of the compound of formula (I), or a pesticidally acceptable salt thereof, ranging up to 80%), wettable powders or granules (including water dispersible granules), particularly those obtained by extrusion, compacting, impregnation of a granular carrier, or granulation starting from a powder (the content of the compound of formula (I), or a pesticidally acceptable salt thereof, in these wettable powders or granules being between about 0.5 and about 80%). Solid homogeneous or heterogeneous compositions containing one or more compounds of formula (I), or pesticidally acceptable salts thereof, for example granules, pellets, briquettes or capsules, may be used to treat standing or running water over a period of time. A similar effect may be achieved using trickle or intermittent feeds of water dispersible concentrates as described herein.

Liquid compositions, for example, include aqueous or non-aqueous solutions or suspensions (such as emulsifiable concentrates, emulsions, flowables, dispersions, or solutions) or aerosols. Liquid compositions also include, in particular, emulsifiable concentrates, dispersions, emulsions, flowables, aerosols, wettable powders (or powder for spraying), dry flowables or pastes as forms of compositions which are liquid or intended to form liquid compositions when applied, for example as aqueous sprays (including low and ultra-low volume) or as fogs or aerosols.

Liquid compositions, for example, in the form of emulsifiable or soluble concentrates most frequently comprise about 5 to about 80% by weight of the activie ingredient, while the emulsions or solutions which are ready for application contain, in their case, about 0.01 to about 20% of the active ingredient. Besides the solvent, the emulsifiable or soluble concentrates may contain, when required, about 2 to about 50% of suitable additives, such as stabilizers, surface-active agents, penetrating agents, corrosion inhibitors, colorants or adhesives. Emulsions of any required concentration, which are particularly suitable for application, for example, to plants, may be obtained from these concentrates by dilution with water. These compositions are included within the scope of the compositions which may be employed in the present invention. The emulsions may be in the form of water-in-oil or oil-in-water type and they may have a thick consistency.

The liquid compositions of this invention may, in addition to normal agricultural use applications be used for example to treat substrates or sites infested or liable to infestation by arthropods (or other pests controlled by compounds of this invention) including premises, outdoor or indoor storage or processing areas, containers or equipment or standing or running water.

All these aqueous dispersions or emulsions or spraying mixtures can be applied, for example, to crops by any suitable means, chiefly by spraying, at rates which are generally of the order of about 100 to about 1,200 liters of spraying mixture per hectare, but may be higher or lower (eg. low or ultra-low volume) depending upon the need or application technique. The compounds or compositions according to the invention are conveniently applied to vegetation and in particular to roots or leaves having pests to be eliminated. Another method of application of the compounds or compositions according to the invention is by chemigation, that is to say, the addition of a formulation containing the active ingredient to irrigation water. This irrigation may be sprinkler irrigation for foliar pesticides or it can be ground irrigation or underground irrigation for soil or for systemic pesticides.

The concentrated suspensions, which can be applied by spraying, are prepared so as to produce a stable fluid product which does not settle (fine grinding) and usually contain from about 10 to about 75% by weight of active ingredient, from about 0.5 to about 30% of surface-active agents, from about 0.1 to about 10% of thixotropic agents, from about 0 to about 30% of suitable additives, such as antifoaming agents, corrosion inhibitors, stabilizers, penetrating agents, adhesives and, as the carrier, water or an organic liquid in which the active ingredient is poorly soluble or insoluble. Some organic solids or inorganic salts may be dissolved in the carrier to help prevent settling or as antifreezes for water.

The wettable powders (or powders for spraying) are usually prepared so that they contain from about 10 to about 80% by weight of active ingredient, from about 20 to about 90% of a solid carrier, from about 0 to about 5% of a wetting agent, from about 3 to about 10% of a dispersing agent and, when necessary, from about 0 to about 80% of one or more stabilizers and/or other additives, such as penetrating agents, adhesives, anti-caking agents, colorants, or the like. To obtain these wettable powders, the active ingredient(s) is(are) thoroughly mixed in a suitable blender with additional substances which may be impregnated on the porous filler and is(are) ground using a mill or other suitable grinder. This produces wettable powders, the wettability and the suspendability of which are advantageous. They may be suspended in water to give any desired concentration and this suspension can be employed very advantageously in particular for application to plant foliage.

The "water dispersible granules (WG)" (granules which are readily dispersible in water) have compositions which are substantially close to that of the wettable powders. They may be prepared by granulation of formulations described for the wettable powders, either by a wet route (contacting finely divided active ingredient with the inert filler and a little water, e.g. from about 1 to about 20% by weight, or with an aqueous solution of a dispersing agent or binder, followed by drying and screening), or by a dry route (compacting followed by grinding and screening).

The rates and concentrations of the formulated compositions may vary according to the method of application or the nature of the compositions or use thereof. Generally speaking, the compositions for application to control arthropod, plant nematode, heiminth or protozoan pests usually contain from about 0.00001% to about 95%, more particularly from about 0.0005% to about 50% by weight of one or more compounds of formula (I), or pesticidally acceptable salts thereof, or of total active ingredients (that is to say the compound of formula (I), or a pesticidally acceptable salt thereof, together with: other substances toxic to arthropods or plant nematodes, anthelnintics, anticoccidials, synergists, trace elements or stabilizers). The actual compositions employed and their rate of application will be selected to achieve the desired effect(s) by the farmer, livestock producer, medical or veterinary practitioner, pest control operator or other person skilled in the art.

Solid or liquid compositions for application topically to animals, timber, stored products or household goods usually contain from about 0.00005% to about 90%, more particularly from about 0.001% to about 10%, by weight of one or more compounds of formula (I) or pesticidally acceptable salts thereof. For administration to animals orally or parenterally, including percutaneously, solid or liquid compositions, these normally contain from about 0.1% to about 90% by weight of one or more compounds of formula (I) or pesticidally acceptable salts thereof. Medicated feedstuffs normally contain from about 0.001% to about 3% by weight of one or more compounds of formula (I) or pesticidally acceptable salts thereof. Concentrates or supplements for mixing with feedstuffs normally contain from about 5% to about 90%, preferably from about 5% to about 50%, by weight of one or more compounds of formula (I) or pesticidally acceptable salts thereof. Mineral salt licks normally contain from about 0.1% to about 10% by weight of one or more compounds of formula (I) or pesticidally acceptable salts thereof.

Dusts or liquid compositions for application to livestock, goods, premises or outdoor areas may contain from about 0.0001% to about 15%, more especially from about 0.005% to about 2.0%, by weight, of one or more compounds of formula (I) or pesticidally acceptable salts thereof. Suitable concentrations in treated waters are between about 0.0001 ppm and about 20 ppm, more particularly about 0.001 ppm to about 5.0 ppm of one or more compounds of formula (I), or pesticidally acceptable salts thereof, and may be used therapeutically in fish farming with appropriate exposure times. Edible baits may contain from about 0.01% to about 5%, preferably from about 0.01% to about 1.0%, by weight, of one or more compounds of formula (I) or pesticidally acceptable salts thereof.

When administered to vertebrates parenterally, orally or by percutaneous cr other means, the dosage of compounds of formula (I), or pesticidally acceptable salts thereof, will depend upon the species, age, or health of the vertebrate and upon the nature and degree of its actual or potential infestation by arthropod, helminth or protozoan pests. A single dose of about 0.1 to about 100 mg, preferably about 2.0 to about 20.0 mg, per kg body weight of the animal or doses of about 0.01 to about 20.0 mg, preferably about 0.1 to about 5.0 mg, per kg body weight of the animal per day, for sustained medication, are generally suitable by oral or parenteral administration. By use of sustained release formulations or devices, the daily dos;es required over a period of months may be combined and administered to animals on a single occasion.

The following composition EXAMPLES 2A–2M illustrate compositions for use against arthropods, especially mites or insects, plant nematodes, or helminth or protozoan pests which comprise, as active ingredient, compounds of formula (I), or pesticidally acceptable salts thereof, such as those described in the preparative examples. The compositions described in EXAMPLES 2A–2M can each be diluted to give a sprayable composition at concentrations suitable for use in the field. Generic chemical descriptions of the ingredients (for which all of the following percentages are in weight percent), used in the composition EXAMPLES 2A–2M exemplified below, are as follows:

| Trade Name | Chemical Description |
| --- | --- |
| Ethylan BCP | Nonylphenol ethylene oxide condensate |
| Soprophor BSU | Tristyrylphenol ethylene oxide condensate |
| Arylan CA | A 70% w/v solution of calcium dodecylbenzenesulfonate |
| Solvesso 150 | Light $C_{10}$ aromatic solvent |
| Arylan S | Sodium dodecylbenzenesulfonate |
| Darvan No 2 | Sodium lignosulphonate |
| Celite PF | Synthetic magnesium silicate carrier |
| Sopropon T36 | Sodium salts of polycarboxylic acids |
| Rhodigel 23 | Polysaccharide xanthan gum |
| Bentone 38 | Organic derivative of magnesium montmorillonite |
| Aerosil | Microfine silicon dioxide |

EXAMPLE 2A

A water soluble concentrate is prepared with the composition as follows:

| Active ingredient | 7% |
| --- | --- |
| Ethylan BCP | 10% |
| N-methylpyrrolidone | 83% |

To a solution of Ethylan BCP dissolved in a portion of N-methylpyrrolidone is added the active ingredient with heating and stirring until dissolved. The resulting solution is made up to volume with the remainder of the solvent.

EXAMPLE 2B

An emulsifiable concentrate (EC) is prepared with the composition as follows:

| Active ingredient | 25% (max) |
| --- | --- |
| Soprophor BSU | 10% |
| Arylan CA | 5% |
| N-methylpyrrolidone | 50% |
| Solvesso 150 | 10% |

The first three components are dissolved in N-methylpyrrolidone and to this is then added the Solvesso 150 to give the final volume.

EXAMPLE 2C

A wettable powder (WP) is prepared with the composition as follows:

| Active ingredient | 40% |
| --- | --- |
| Arylan S | 2% |
| Darvan No2 | 5% |
| Celite PF | 53% |

The ingredients are mixed and ground in a hammer-mill to a powder with a particle size of less than 50 microns.

EXAMPLE 2D

An aqueous-flowable formulation is prepared with the composition as follows:

| Active ingredient | 40.00% |
| --- | --- |
| Ethylan BCP | 1.00% |
| Sopropon T360 | 0.20% |
| Ethylene glycol | 5.00% |
| Rhodigel 230 | 0.15% |
| Water | 53.65% |

The ingredients are intimately mixed and are ground in a bead mill until a mean particle size of less than 3 microns is obtained.

EXAMPLE 2E

An emulsifiable suspension concentrate is prepared with the composition as follows:

| Active ingredient | 30.0% |
| --- | --- |
| Ethylan BCP | 10.0% |
| Bentone 38 | 0.5% |
| Solvesso 150 | 59.5% |

The ingredients are intimately mixed and ground in a beadmill until a mean particle size of less than 3 microns is obtained.

EXAMPLE 2F

A water dispersible granule is prepared with the composition as follows:

| Active ingredient | 30% |
| --- | --- |
| Darvan No 2 | 15% |
| Arylan S | 8% |
| Celite PF | 47% |

The ingredients are mixed, micronized in a fluid-energy mill and then granulated in a rotating pelletizer by spraying with water (up to 10%). The resulting granules are dried in a fluid-bed drier to remove excess water.

EXAMPLE 2G

A dusting powder is prepared with the composition as follows:

| Active ingredient | 1 to 10% |
|---|---|
| Talc powder-superfine | 99 to 90% |

The ingredients are intimately mixed and further ground as necessary to achieve a fme powder. This powder may be applied to a locus of arthropod infestation, for example refuse dumps, stored products or household goods or animals infested by, or at risk of infestation by, arthropods to control the arthropods by oral ingestion. Suitable means for distributing the dusting powder to the locus of arthropod infestation include mechanical blowers, handshakers or livestock self treatment devices.

EXAMPLE 2H

An edible bait is prepared with the composition as follows:

| Active ingredient | 0.1 to 1.0% |
|---|---|
| Wheat flour | 80% |
| Molasses | 19.9 to 19% |

The ingredients are intimately mixed and formed as required into a bait form. This edible bait may be distributed at a locus, for example domestic or industrial premises, e.g. kitchens, hospitals or stores, or outdoor areas, infested by arthropods, for example ants, locusts, cockroaches or flies, to control the arthropods by oral ingestion.

EXAMPLE 2I

A solution formulation is prepared with a composition as follows:

| Active ingredient | 15% |
|---|---|
| Dimethyl sulfoxide | 85% |

The active ingredient is dissolved in dimethyl sulfoxide with mixing and/or heating as required. This solution may be applied percutaneously as a pour-on application to domestic animals infested by arthropods or, after sterilization by filtration through a polytetrafluoroethylene membrane (0.22 micrometer pore size), by parenteral injection, at a rate of application of from 1.2 to 12 ml of solution per 100 kg of animal body weight.

EXAMPLE 2J

A wettable powder is prepared with the composition as follows:

| Active ingredient | 50% |
|---|---|
| Ethylan BCP | 5% |
| Aerosil | 5% |
| Celite PF | 40% |

The Ethylan BCP is absorbed onto the Aerosil which is then mixed with the other ingredients and ground in a hammer-mill to give a wettable powder, which may be diluted with water to a concentration of from 0.001% to 2% by weight of the active compound and applied to a locus of infestation by arthropods, for example, dipterous larvae or plant nematodes, by spraying, or to domestic animals infested by, or at risk of infection by arthropods, helminths or protozoa, by spraying or dipping, or by oral administration in drinking water, to control the arthropods, helminths or protozoa.

EXAMPLE 2K

A slow release bolus composition is formed from granules containing the following components in varying percentages (similar to those described for the previous compositions) depending upon need:

| Active ingredient |
|---|
| Density agent |
| Slow-release agent |
| Binder |

The intimately mixed ingredients are formed into granules which are compressed into a bolus with a specific gravity of 2 or more. This can be a administered orally to ruminant domestic animals for retention within the reticulorumen to give a continual slow release of active compound over an extended period of time to control infestation of the ruminant domestic animals by arthropods, helminths or protozoa.

EXAMPLE 2L

A slow release composition in the form of granules, pellets, brickettes or the like can be prepared with compositions as follows:

| Active ingredient | 0.5 to 25% |
|---|---|
| Polyvinyl chloride | 75 to 99.5% |
| Dioctyl phthalate (plasticizer) | |

The components are blended and then formed into suitable shapes by meltextrusion or molding. These composition are useful, for example, for addition to standing water or for fabrication into collars or eartags for attachment to domestic animals to control pests by slow release.

EXAMPLE 2M

A water dispersible granule is prepared with the composition as follows:

| Active ingredient | 85% (max) |
|---|---|
| Polyvinylpyrrolidone | 5% |
| Attapulgite clay | 6% |
| Sodium lauryl sulfate | 2% |
| Glycerine | 2% |

The ingredients are mixed as a 45% slurry with water and wet milled to a particle size of 4 microns, then spray-dried to remove water.

While the invention has been described in terms of various preferred embodiments, the skilled artisan will appreciate that various modifications, substitutions, omissions and changes can be made without departing from the spirit thereof. Accordingly, it is intended that the scope of the present invention be limited solely by the scope of the following claims, including equivalents thereof.

What we claim is:

1. A compound having the formula:

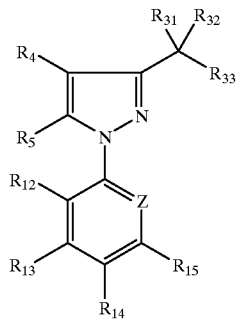

(I)

or a pesticidally acceptable salt thereof, wherein:

$R_{31}$ and $R_{32}$, which are the same or different, are each $OR_{20}$, $S(O)_nR_{20}$, or $N(R_{20})(R_{21})$; or $R_{31}$ and $R_{32}$ are combined to form $O[C(R_{22})(R_{23})]_mO$, $S(O)_n[C(R_{22})(R_{23})]_mS(O)_a$, $O(CH_2)_mS(O)_a$, $O[C(R_{22})(R_{23})]_m(NR_{20})$, $S(O)_n[C(R_{22})(R_{23})]_m(NR_{20})$, $NR_{21}[C(R_{22})(R_{23})]_mNR_{20}$, or $NR_{21}[C(O)(CH_2)_m]NR_{20}$;

m is an integer from 1 to 5 inclusive;

when m is greater than one, then the groups $[C(R_{22})(R_{23})]$ are the same or different;

$R_{20}$ and $R_{21}$, which are the same or different, are each H, $C_1$–$C_6$ alkyl, benzyl, allyl, propargyl, or $C_6$–$C_{10}$ aryl optionally bearing one or more substituents selected from the group consisting of halogen, $C_1$–$C_6$ alkyl, $C_1$–$C_6$ alkoxy, CN, $NO_2$, $C_1$–$C_6$ haloalkyl and $C_1$–$C_6$ haloalkoxy;

$R_{22}$ and $R_{23}$, which are the same or different, are each H; halogen; OH; $NH_2$; $COOR_{20}$; $C(O)NH_2$; $C(O)N(R_{20})(R_{21})$; $C(S)NH_2$; $OC(O)N(R_{20})(R_{21})$; CN; $NO_2$; $C(S)N(R_{20})(R_{21})$; or $C_1$–$C_6$ alkyl, which optionally bears one or more substituents selected from the group consisting of OH, $NH_2$, halogen, CN, $NO_2$, $COOR_{20}$, $C(O)NH_2$, $C(S)NH_2$, $C_1$–$C_6$ $S(O)_b$alkyl, $C_1$–$C_6$ alkoxy, and $S(O)_cR_{20}$;

$R_4$ is $R_{26}$; $S(O)_dR_{26}$; or $S(=R_{27})(=NR_{28})R_{26}$;

$R_{26}$ is $C_1$–$C_6$ alkyl, optionally substituted with one or more halogen which are the same or different;

$R_5$ is a radical having the formula:

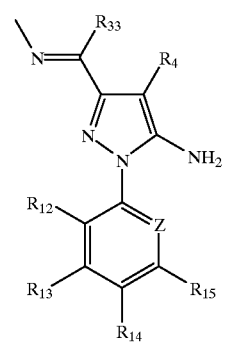

(Ia)

wherein $R_4$, $R_{12}$, $R_{13}$, $R_{14}$, $R_{15}$, Z and $R_{33}$ are identical to $R_4$, $R_{12}$, $R_{13}$, $R_{14}$, $R_{15}$, Z and $R_{33}$, respectively, in formula (I) above;

$R_{27}$ is $NR_{28}$, O or a lone pair of electrons;

$R_{28}$ is H; $C_1$–$C_6$ alkyl; $C_1$–$C_6$ haloalkyl; $COR_{24}$; $S(O)_eR_{24}$; $COOR_{24}$;
$C(O)N(R_{20})(R_{21})$; $C(O)SR_{24}$; $C(S)OR_{24}$; $SO_2NR_{20}R_{21}$; $P(O)_q(R_{20})(R_{21})$;
$P(O)_q(OR_{20})(OR_{21})$; $C(=NR_{20})NR_{20}R_{21}$; $C(=NR_{20})(OR_{21})$; $C(S)N(R_{20})(R_{21})$;
$C(O)C(O)R_{20}$; $C(O)C(O)OR_{20}$; $C(O)C(O)NR_{20}R_{21}$; or $C(O)NR_{20}SO_2R_{21}$;

q is 0 or 1;

$R_{24}$ is $C_1$–$C_6$ alkyl, optionally bearing one or more substituents selected from the group consisting of $NO_2$, CN, halogen, $C_1$–$C_6$ alkoxy, amino, ($C_1$–$C_6$ alkoxy)carbonyl and OH;

Z is
C—$R_{16}$;

$R_{12}$, $R_{13}$, $R_{14}$, $R_{15}$ and $R_{16}$, which are the same or different, are each H;
halogen; $SF_5$; CN; $NO_2$; $R_{25}$; $S(O)_fR_{25}$; OH; $OR_{25}$; $N(R_{36})(R_{37})$; $CON(R_{25})(R_{37})$;
or $N_3$ (azido);

$R_{36}$ and $R_{37}$, which are the same or different, are each H or $C_1$–$C_6$ alkyl;

$R_{25}$ is $C_1$–$C_6$ alkyl, optionally substituted with one or more halogen which are the same or different; and $R_{33}$ is $C_1$ to $C_3$ alkyl, optionally bearing one or more substituents selected from the group consisting of halogen, $NO_2$, $C_1$–$C_6$ alkoxy, CN, COOH, COO ($C_1$–$C_6$ alkyl), and $C(O)NH_2$; and n, a, b, c, d, e and f, which are the same or different, are each 0, 1 or 2.

2. A compound according to claim 1, wherein m is 2, 3 or 4.

3. A compound according to claim 2, wherein m is 2 or 3.

4. A compound according to claim 3, wherein m is 2.

5. A compound having the formula:

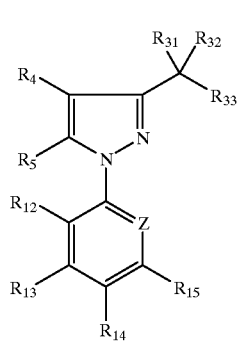

(I)

or a pesticidally acceptable salt thereof, wherein:

$R_{31}$ and $R_{32}$, which are the same or different, are each $OCH_3$, $OC_2H_5$, $S(O)_mCH_3$ or $S(O)_nC_2H_5$; or $R_{31}$ and $R_{32}$ are combined to form $OCH_2CH_2O$, $O(CH_2)_3O$, $S(CH_2)_2S$, $S(O)(CH_2)_2S$, $S(O)(CH_2)_2S(O)$, $S(O)_2(CH_2)_2S(O)$, $S(O)_2(CH_2)_2S(O)_2$, $S(CH_2)_2O$, $S(O)(CH_2)_2O$, $S(O)_2(CH_2)_2O$, $O(CH_2)[CH(CH_2OH)]O$, $O(CH_2)[C(CH_2OH)(CH_2OH)]O$, $OCH(COOCH_3)CH(COOCH_3)O$, $OCH(COOC_2H_5)CH(COOC_2H_5)O$, $OCH_2C(COOCH_3)(COOCH_3)CH_2O$, $OCH_2C(COOC_2H_5)(COOC_2H_5)CH_2O$, $OCH_2CH(CH_3)O$, $SCH_2CH_2NH$, $OCH_2CH(CH_2CH_2OH)O$, $OCH_2C(CH_2OH)_2CH_2O$, $OCH_2CH(CH_2SCH_3)O$ or $OCH_2CH(CH_2SOCH_3)O$;

$R_4$ is $R_{26}$; $S(O)_dR_{26}$; or $S(=R_{27})(=NR_{28})R_{26}$;

$R_{26}$ is $C_1$–$C_6$ alkyl, optionally substituted with one or more halogen which are the same or different;

$R_5$ is a radical of the formula:

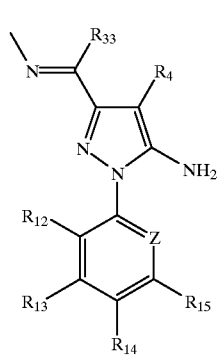

(Ia)

wherein $R_4$, $R_{12}$, $R_{13}$, $R_{14}$, $R_{15}$, Z and $R_{33}$ are identical to $R_4$, $R_{12}$, $R_{13}$, $R_{14}$, $R_{15}$, Z and $R_{33}$, respectively, in formula (I) above;

$R_{27}$ is $NR_{28}$, O or a lone pair of electrons;

$R_{28}$ is H; $C_1$–$C_6$ alkyl; $C_1$–$C_6$ haloalkyl; $COR_{24}$; $S(O)_eR_{24}$; $COOR_{24}$;
$C(O)N(R_{20})(R_{21})$; $C(O)SR_{24}$; $C(S)OR_{24}$; $SO_2NR_{20}R_{21}$; $P(O)_q(R_{20})(R_{21})$;
$P(O)_q(OR_{20})(OR_{21})$; $C(=NR_{20})NR_{20}R_{21}$; $C(=NR_{20})(OR_{21})$; $C(S)N(R_{20})(R_{21})$;
$C(O)C(O)R_{20}$; $C(O)C(O)OR_{20}$; $C(O)C(O)NR_{20}R_{21}$; or $C(O)NR_{20}SO_2R_{21}$;

q is 0 or 1;

$R_{20}$ and $R_{21}$, which are the same or different, are each H, $C_1$–$C_6$ alkyl, benzyl, allyl, propargyl, or $C_6$–$C_{10}$ aryl optionally bearing one or more substituents selected from the group consisting of halogen, $C_1$–$C_6$ alkyl, $C_1$–$C_6$ alkoxy, CN, $NO_2$, $C_1$–$C_6$ haloalkyl and $C_1$–$C_6$ haloalkoxy;

$R_{24}$ is $C_1$–$C_6$ alkyl, optionally bearing one or more substituents selected from the group consisting of $NO_2$, CN, halogen, $C_1$–$C_6$ alkoxy, amino, ($C_1$–$C_6$ alkoxy)carbonyl and OH;

Z is

C—$R_{16}$;

$R_{12}$, $R_{13}$, $R_{14}$, $R_{15}$ and $R_{16}$, which are the same or different, are each H;

halogen; $SF_5$; CN; $NO_2$; $R_{25}$; $S(O)_fR_{25}$; OH; $OR_{25}$; $N(R_{36})(R_{37})$; $CON(R_{25})(R_{37})$;
or $N_3$ (azido);

$R_{36}$ and $R_{37}$, which are the same or different, are each H or $C_1$–$C_6$ alkyl;

$R_{25}$ is $C_1$–$C_6$ alkyl, optionally substituted with one or more halogen which are the same or different; and $R_{33}$ is $C_1$ to $C_3$ alkyl, optionally bearing one or more substituents selected from the group consisting of halogen, $NO_2$, $C_1$–$C_6$ alkoxy, CN, COOH, COO ($C_1$–$C_6$ alkyl), and $C(O)NH_2$; and n, d, e and f, which are the same or different, are each 0, 1 or 2.

6. A compound according to claim 5, wherein $R_{13}$ and $R_{15}$, which are the same or different, are each H or halogen.

7. A compound according to claim 5, wherein $R_{12}$ is halogen.

8. A compound according to claim 5, wherein $R_{14}$ is halogen, $SF_5$, $R_{25}$, $S(O)_fR_{25}$ or $OR_{25}$.

9. A compound according to claim 5, wherein $R_{12}$ is chlorine, $R_{13}$ and $R_{15}$ are each H, $R_{14}$ is $CF_3$ and Z is C—Cl.

10. A compound according to claim 5, wherein $R_{13}$ and $R_{15}$, which are the same or different, are each H or halogen; $R_{12}$ is halogen; $R_{16}$ is H or halogen; and $R_{14}$ is halogen, $SF_5$, $R_{25}$, $S(O)_fR_{25}$ or $OR_{25}$.

11. A compound according to claim 5, wherein $R_4$ is $S(O)_dR_{26}$.

12. A compound according to claim 5, wherein $R_{26}$ is $CH_3$ or $CH_2CH_3$.

13. A compound according to claim 5, wherein $R_{13}$ and $R_{15}$ are H.

14. A compound according to claim 5, wherein $R_{14}$ is $CF_3$, $OCF_3$ or $SF_5$.

15. A compound according to claim 5, wherein $R_{33}$ is $CH_3$.

16. A compound according to claim 5, wherein $R_{26}$ is $CH_3$ or $CH_2CH_3$;

$R_{13}$ and $R_{15}$ are each H; $R_{12}$ is halogen; $R_{16}$ is H or halogen; $R_{14}$ is $CF_3$, $OCF_3$ or $SF_5$; and $R_{33}$ is $CH_3$.

17. A compound according to claim 5, wherein $R_{31}$ and $R_{32}$, which are the same or different, are each $OCH_3$, $OC_2H_5$, $SCH_3$ or $SC_2H_5$.

18. A compound according to claim 5, wherein $R_{31}$ and $R_{32}$ are each $OCH_3$.

19. A compound according to claim 5, wherein $R_{31}$ and $R_{32}$ are combined to form $OCH_2CH_2O$, $O(CH_2)_3O$, $S(CH_2)_2S$, $S(O)(CH_2)_2S$, $S(O)(CH_2)_2S(O)$, $S(O)_2(CH_2)_2S(O)$, $S(O)_2(CH_2)_2S(O)_2$, $S(CH_2)_2O$, $S(O)(CH_2)_2O$, $S(O)_2(CH_2)_2O$, $O(CH_2)[CH(CH_2OH)]O$, $O(CH_2)[C(CH_2OH)(CH_2OH)]O$, $OCH(COOCH_3)CH(COOCH_3)O$, $OCH(COOC_2H_5)CH(COOC_2H_5)O$, $OCH_2C(COOCH_3)(COOCH_3)CH_2O$, $OCH_2C(COOC_2H_5)(COOC_2H_5)CH_2O$, $OCH_2CH(CH_3)O$, $SCH_2CH_2NH$, $OCH_2CH(CH_2CH_2OH)O$, $OCH_2C(CH_2OH)_2CH_2O$, $OCH_2CH(CH_2SCH_3)O$ or $OCH_2CH(CH_2SOCH_3)O$.

20. A compound according to claim 5, wherein $R_{31}$ and $R_{32}$, which are the same or different, are each $OCH_3$, $OC_2H_5$, $SCH_3$ or $SC_2H_5$; or $R_{31}$ and $R_{32}$ are combined to form $OCH_2CH_2O$, $O(CH_2)_3O$, $S(CH_2)_2S$, $S(O)(CH_2)_2S$, $S(O)(CH_2)_2S(O)$, $S(O)_2(CH_2)_2S(O)$, $S(O)_2(CH_2)_2S(O)_2$, $S(CH_2)_2O$, $S(O)(CH_2)_2O$, $S(O)_2(CH_2)_2O$, $O(CH_2)[CH(CH_2OH)]O$, $O(CH_2)[C(CH_2OH)(CH_2OH)]O$, $OCH(COOCH_3)CH(COOCH_3)O$, $OCH(COOC_2H_5)CH(COOC_2H_5)O$, $OCH_2C(COOCH_3)(COOCH_3)CH_2O$, $OCH_2C(COOC_2H_5)(COOC_2H_5)CH_2O$, $OCH_2CH(CH_3)O$, $SCH_2CH_2NH$, $OCH_2CH(CH_2CH_2OH)O$, $OCH_2C(CH_2OH)_2CH_2O$, $OCH_2CH(CH_2SCH_3)O$ or $OCH_2CH(CH_2SOCH_3)O$; $R_4$ is $S(O)_dR_{26}$; $R_{26}$ is $CH_3$ or $CH_2CH_3$; $R_{13}$ and $R_{15}$ are each H; $R_{12}$ is halogen; $R_{16}$ is H or halogen; $R_{14}$ is $CF_3$, $OCF_3$ or $SF_5$; and $R_{33}$ is $CH_3$.

21. The compound according to claim 5, having the formula:

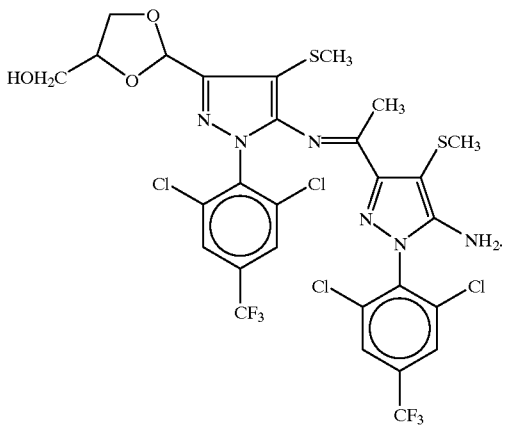

22. A method of controlling pests at a locus which comprises applying to said locus a pesticidally effective amount of a compound as claimed in claim 1, or a pesticidally acceptable salt thereof.

23. A method of controlling pests at a locus which comprises applying to said locus a pesticidally effective amount of a compound as claimed in claim 5, or a pesticidally acceptable salt thereof.

24. A method according to claim 23, wherein the pests are insects and an insecticidally effective amnount of the compound of formnula (I) is applied.

25. A method according to claim 24, wherein the insects are sucking insects.

26. A method according to claim 23, wherein the locus is an area used or to be used for the growing of crops.

27. A method according to claim 26, wherein the compound of formula (I) is applied at a rate of from about 5 g to about 1 kg/ha.

28. A method according to claim 23, wherein the locus is an animal.

29. A method according to claim 28, wherein the compound of formula (I) is applied at a rate of from about 0.1 to about 20 mg per kg body weight of animal per day.

30. A pesticidal composition comprising a pesticidally effective amount of a compound of formula (I) as claimed in claim 1, or a pesticidally acceptable salt thereof, and a pesticidally acceptable diluent or carrier therefor.

31. A pesticidal composition comprising a pesticidally effective amount of a compound of formula (I) as claimed in claim 5, or a pesticidally acceptable salt thereof, and a pesticidally acceptable diluent or carrier therefor.

32. A pesticidal composition according to claim 31, comprising from about 0.05% to about 95% by weight of a compound of formula (I).

33. An insecticidal composition comprising an insecticidally effective amount of a compound of formula (I) as claimed in claim 1, or an insecticidally acceptable salt thereof, and an insecticidally acceptable diluent or carrier therefor.

34. An insecticidal composition comprising an insecticidally effective amount of a compound of formula (I) as claimed in claim 5, or an insecticidally acceptable salt thereof, and an insecticidaily acceptable diluent or carrier therefor.

35. A process for the preparation of a compound of formula (I) as claimed in claim 1, said process comprising reacting a compound having the formula:

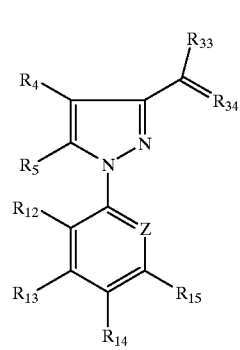

(II)

wherein $R_4$, $R_5$, $R_{12}$, $R_{13}$, $R_{14}$, $R_{15}$, Z and $R_{33}$ are as defined in claim 5 and $R_{34}$ is oxygen or sulfur, with an alcohol having the formula $CH_3OH$ or $C_2H_5OH$, a thiol having the formula $CH_3SH$ or $C_2H_5SH$, or a compound having the formula $HOCH_2CH_2OH$, $HO(CH_2)_3OH$, $HS(CH_2)_2SH$, $HS(CH_2)_2OH$, $HOCH_2[CH(CH_2OH)]OH$, $HOCH_2[C(CH_2OH)(CH_2OH)]OH$, $HOCH(COOCH_3)CH(COOCH_3)OH$, $HOCH(COOC_2H_5)CH(COOC_2H_5)OH$, $HOCH_2C(COOCH_3)(COOCH_3)CH_2OH$, $HOCH_2CH(COOC_2H_5)(COOC_2H_5)CH_2OH$, $HOCH_2CH(CH_3)OH$, $HSCH_2CH_2NH_2$, $HOCH_2CH(CH_2CH_2OH)OH$, $HOCH_2C(CH_2OH)_2CH_2OH$ or $HOCH_2CH(CH_2SCH_3)OH$;

followed by, if desired, oxidation of a resultant compound of formula (I) having one or two thio groups to the corresponding compound of formula (I) having one or two sulfmyl or sulfonyl groups.

* * * * *